(12) United States Patent
Diab

(10) Patent No.: US 7,791,155 B2
(45) Date of Patent: Sep. 7, 2010

(54) DETECTOR SHIELD

(75) Inventor: Mohamed K. Diab, Ladera Ranch, CA (US)

(73) Assignee: Masimo Laboratories, Inc., Irvine, CA (US)

( * ) Notice: Subject to any disclaimer, the term of this patent is extended or adjusted under 35 U.S.C. 154(b) by 320 days.

(21) Appl. No.: 11/963,518

(22) Filed: Dec. 21, 2007

(65) Prior Publication Data

US 2008/0197301 A1 Aug. 21, 2008

Related U.S. Application Data

(60) Provisional application No. 60/876,758, filed on Dec. 22, 2006.

(51) Int. Cl.
*H01L 31/0232* (2006.01)
(52) U.S. Cl. .................. 257/435; 257/434; 257/660; 257/708; 257/E23.114; 438/65; 438/72; 250/506.1; 250/515.1
(58) Field of Classification Search ................ 257/435, 257/434, 660, 708, E23.114; 438/65, 72; 250/506.1, 515.1
See application file for complete search history.

(56) References Cited

U.S. PATENT DOCUMENTS

| 4,960,128 | A | 10/1990 | Gordon et al. |
| 4,964,408 | A | 10/1990 | Hink et al. |
| 5,041,187 | A | 8/1991 | Hink et al. |
| 5,069,213 | A | 12/1991 | Polczynski |
| 5,163,438 | A | 11/1992 | Gordon et al. |
| 5,337,744 | A | 8/1994 | Branigan |
| 5,341,805 | A | 8/1994 | Stavridi et al. |
| D353,195 | S | 12/1994 | Savage et al. |
| D353,196 | S | 12/1994 | Savage et al. |
| 5,377,676 | A | 1/1995 | Vari et al. |
| D359,546 | S | 6/1995 | Savage et al. |
| 5,431,170 | A | 7/1995 | Mathews |
| D361,840 | S | 8/1995 | Savage et al. |
| D362,063 | S | 9/1995 | Savage et al. |
| 5,452,717 | A | 9/1995 | Branigan et al. |
| D363,120 | S | 10/1995 | Savage et al. |
| 5,456,252 | A | 10/1995 | Vari et al. |
| 5,482,036 | A | 1/1996 | Diab et al. |
| 5,490,505 | A | 2/1996 | Diab et al. |
| 5,494,043 | A | 2/1996 | O'Sullivan et al. |
| 5,533,511 | A | 7/1996 | Kaspari et al. |

(Continued)

*Primary Examiner*—Tu-Tu V Ho
(74) *Attorney, Agent, or Firm*—Knobbe Martens Olson & Bear LLP

(57) ABSTRACT

An improved photodiode detector shielding apparatus and method are provided which shield a photodiode detector from electromagnetic interference and ambient light, without affecting the wavelengths of light that reach the photodiode. The improved photodiode detector shield has two layers. A bottom layer is substantially made from an electrically conducting material and is fixed over a photodiode in order to shield it from EMI and ambient light. A top layer is substantially made from a lustrous, shiny, reflective material that reflects an equal amount of light across a band of wavelengths. Both layers have areas with optically transmissive openings, which are aligned to allow for the unobstructed passage of light of a band of wavelengths to the photodiode. Light within a band of wavelengths is evenly reflected off the top of the first surface and also reaches the photodiode. In this regard, the detector shield blocks EMI and ambient light without affecting the wavelengths of light desired to reach the photodiode.

16 Claims, 12 Drawing Sheets

U.S. PATENT DOCUMENTS

| | | | |
|---|---|---|---|
| 5,561,275 A | 10/1996 | Savage et al. | |
| 5,562,002 A | 10/1996 | Lalin | |
| 5,576,239 A * | 11/1996 | Hatano et al. | 438/69 |
| 5,590,649 A | 1/1997 | Caro et al. | |
| 5,602,924 A | 2/1997 | Durand et al. | |
| 5,619,059 A * | 4/1997 | Li et al. | 257/431 |
| 5,632,272 A | 5/1997 | Diab et al. | |
| 5,638,816 A | 6/1997 | Kiani-Azarbayjany et al. | |
| 5,638,818 A | 6/1997 | Diab et al. | |
| 5,645,440 A | 7/1997 | Tobler et al. | |
| 5,685,299 A | 11/1997 | Diab et al. | |
| D393,830 S | 4/1998 | Tobler et al. | |
| 5,743,262 A | 4/1998 | Lepper, Jr. et al. | |
| 5,758,644 A | 6/1998 | Diab et al. | |
| 5,760,910 A | 6/1998 | Lepper, Jr. et al. | |
| 5,769,785 A | 6/1998 | Diab et al. | |
| 5,782,757 A | 7/1998 | Diab et al. | |
| 5,785,659 A | 7/1998 | Caro et al. | |
| 5,791,347 A | 8/1998 | Flaherty et al. | |
| 5,810,734 A | 9/1998 | Caro et al. | |
| 5,823,950 A | 10/1998 | Diab et al. | |
| 5,830,131 A | 11/1998 | Caro et al. | |
| 5,833,618 A | 11/1998 | Caro et al. | |
| 5,860,919 A | 1/1999 | Kiani-Azarbayjany et al. | |
| 5,890,929 A | 4/1999 | Mills et al. | |
| 5,904,654 A | 5/1999 | Wohltmann et al. | |
| 5,919,134 A | 7/1999 | Diab | |
| 5,934,925 A | 8/1999 | Tobler et al. | |
| 5,940,182 A | 8/1999 | Lepper, Jr. et al. | |
| 5,995,855 A | 11/1999 | Kiani et al. | |
| 5,997,343 A | 12/1999 | Mills et al. | |
| 6,002,952 A | 12/1999 | Diab et al. | |
| 6,011,986 A | 1/2000 | Diab et al. | |
| 6,027,452 A | 2/2000 | Flaherty et al. | |
| 6,036,642 A | 3/2000 | Diab et al. | |
| 6,045,509 A | 4/2000 | Caro et al. | |
| 6,067,462 A | 5/2000 | Diab et al. | |
| 6,081,735 A | 6/2000 | Diab et al. | |
| 6,088,607 A | 7/2000 | Diab et al. | |
| 6,110,522 A | 8/2000 | Lepper, Jr. et al. | |
| 6,124,597 A | 9/2000 | Shehada et al. | |
| 6,144,868 A | 11/2000 | Parker | |
| 6,151,516 A | 11/2000 | Kiani-Azarbayjany et al. | |
| 6,152,754 A | 11/2000 | Gerhardt et al. | |
| 6,157,850 A | 12/2000 | Diab et al. | |
| 6,165,005 A | 12/2000 | Mills et al. | |
| 6,184,521 B1 | 2/2001 | Coffin, IV et al. | |
| 6,206,830 B1 | 3/2001 | Diab et al. | |
| 6,229,856 B1 | 5/2001 | Diab et al. | |
| 6,232,609 B1 | 5/2001 | Snyder et al. | |
| 6,236,872 B1 | 5/2001 | Diab et al. | |
| 6,241,683 B1 | 6/2001 | Macklem et al. | |
| 6,256,523 B1 | 7/2001 | Diab et al. | |
| 6,263,222 B1 | 7/2001 | Diab et al. | |
| 6,278,522 B1 | 8/2001 | Lepper, Jr. et al. | |
| 6,280,213 B1 | 8/2001 | Tobler et al. | |
| 6,285,896 B1 | 9/2001 | Tobler et al. | |
| 6,321,100 B1 | 11/2001 | Parker | |
| 6,334,065 B1 | 12/2001 | Al-Ali et al. | |
| 6,343,224 B1 | 1/2002 | Parker | |
| 6,349,228 B1 | 2/2002 | Kiani et al. | |
| 6,360,114 B1 | 3/2002 | Diab et al. | |
| 6,368,283 B1 | 4/2002 | Xu et al. | |
| 6,371,921 B1 | 4/2002 | Caro et al. | |
| 6,377,829 B1 | 4/2002 | Al-Ali | |
| 6,388,240 B2 | 5/2002 | Schulz et al. | |
| 6,397,091 B2 | 5/2002 | Diab et al. | |
| 6,430,525 B1 | 8/2002 | Weber et al. | |
| 6,463,311 B1 | 10/2002 | Diab | |
| 6,470,199 B1 | 10/2002 | Kopotic et al. | |
| 6,501,975 B2 | 12/2002 | Diab et al. | |
| 6,505,059 B1 | 1/2003 | Kollias et al. | |
| 6,515,273 B2 | 2/2003 | Al-Ali | |
| 6,519,487 B1 | 2/2003 | Parker | |
| 6,525,386 B1 | 2/2003 | Mills et al. | |
| 6,526,300 B1 | 2/2003 | Kiani et al. | |
| 6,541,756 B2 | 4/2003 | Schulz et al. | |
| 6,542,764 B1 | 4/2003 | Al-Ali et al. | |
| 6,580,086 B1 | 6/2003 | Schulz et al. | |
| 6,584,336 B1 | 6/2003 | Ali et al. | |
| 6,595,316 B2 | 7/2003 | Cybulski et al. | |
| 6,597,932 B2 | 7/2003 | Tian et al. | |
| 6,597,933 B2 | 7/2003 | Kiani et al. | |
| 6,606,511 B1 | 8/2003 | Ali et al. | |
| 6,632,181 B2 | 10/2003 | Flaherty et al. | |
| 6,639,668 B1 | 10/2003 | Trepagnier | |
| 6,640,116 B2 | 10/2003 | Diab | |
| 6,643,530 B2 | 11/2003 | Diab et al. | |
| 6,650,917 B2 | 11/2003 | Diab et al. | |
| 6,654,624 B2 | 11/2003 | Diab et al. | |
| 6,658,276 B2 | 12/2003 | Pishney et al. | |
| 6,661,161 B1 | 12/2003 | Lanzo et al. | |
| 6,671,531 B2 | 12/2003 | Al-Ali et al. | |
| 6,678,543 B2 | 1/2004 | Diab et al. | |
| 6,684,090 B2 | 1/2004 | Ali et al. | |
| 6,684,091 B2 | 1/2004 | Parker | |
| 6,697,656 B1 | 2/2004 | Al-Ali | |
| 6,697,657 B1 | 2/2004 | Shehada et al. | |
| 6,697,658 B2 | 2/2004 | Al-Ali | |
| RE38,476 E | 3/2004 | Diab et al. | |
| 6,699,194 B1 | 3/2004 | Diab et al. | |
| 6,714,804 B2 | 3/2004 | Al-Ali et al. | |
| RE38,492 E | 4/2004 | Diab et al. | |
| 6,721,582 B2 | 4/2004 | Trepagnier et al. | |
| 6,721,585 B1 | 4/2004 | Parker | |
| 6,725,075 B2 | 4/2004 | Al-Ali | |
| 6,728,560 B2 | 4/2004 | Kollias et al. | |
| 6,735,459 B2 | 5/2004 | Parker | |
| 6,745,060 B2 | 6/2004 | Diab et al. | |
| 6,760,607 B2 | 7/2004 | Al-All | |
| 6,770,028 B1 | 8/2004 | Ali et al. | |
| 6,771,994 B2 | 8/2004 | Kiani et al. | |
| 6,792,300 B1 | 9/2004 | Diab et al. | |
| 6,813,511 B2 | 11/2004 | Diab et al. | |
| 6,816,741 B2 | 11/2004 | Diab | |
| 6,822,564 B2 | 11/2004 | Al-Ali | |
| 6,826,419 B2 | 11/2004 | Diab et al. | |
| 6,830,711 B2 | 12/2004 | Mills et al. | |
| 6,850,787 B2 | 2/2005 | Weber et al. | |
| 6,850,788 B2 | 2/2005 | Al-Ali | |
| 6,852,083 B2 | 2/2005 | Caro et al. | |
| 6,861,639 B2 | 3/2005 | Al-Ali | |
| 6,898,452 B2 | 5/2005 | Al-Ali et al. | |
| 6,920,345 B2 | 7/2005 | Al-Ali et al. | |
| 6,931,268 B1 | 8/2005 | Kiani-Azarbayjany et al. | |
| 6,934,570 B2 | 8/2005 | Kiani et al. | |
| 6,939,305 B2 | 9/2005 | Flaherty et al. | |
| 6,943,348 B1 | 9/2005 | Coffin, IV | |
| 6,950,687 B2 | 9/2005 | Al-Ali | |
| 6,961,598 B2 | 11/2005 | Diab | |
| 6,970,792 B1 | 11/2005 | Diab | |
| 6,979,812 B2 | 12/2005 | Al-Ali | |
| 6,985,764 B2 | 1/2006 | Mason et al. | |
| 6,993,371 B2 | 1/2006 | Kiani et al. | |
| 6,996,427 B2 | 2/2006 | Ali et al. | |
| 6,999,904 B2 | 2/2006 | Weber et al. | |
| 7,003,338 B2 | 2/2006 | Weber et al. | |
| 7,003,339 B2 | 2/2006 | Diab et al. | |
| 7,015,451 B2 | 3/2006 | Dalke et al. | |
| 7,024,233 B2 | 4/2006 | Ali et al. | |
| 7,027,849 B2 | 4/2006 | Al-Ali | |
| 7,030,749 B2 | 4/2006 | Al-Ali | |
| 7,039,449 B2 | 5/2006 | Al-Ali | |
| 7,041,060 B2 | 5/2006 | Flaherty et al. | |

| | | | | | | |
|---|---|---|---|---|---|---|
| 7,044,918 | B2 | 5/2006 | Diab | 7,254,434 B2 | 8/2007 | Schulz et al. |
| 7,067,893 | B2 | 6/2006 | Mills et al. | 7,272,425 B2 | 9/2007 | Al-Ali |
| 7,096,052 | B2 | 8/2006 | Mason et al. | 7,274,955 B2 | 9/2007 | Kiani et al. |
| 7,096,054 | B2 | 8/2006 | Abdul-Hafiz et al. | D554,263 S | 10/2007 | Al-Ali |
| 7,132,641 | B2 | 11/2006 | Schulz et al. | 7,280,858 B2 | 10/2007 | Al-Ali et al. |
| 7,142,901 | B2 | 11/2006 | Kiani et al. | 7,289,835 B2 | 10/2007 | Mansfield et al. |
| 7,149,561 | B2 | 12/2006 | Diab | 7,292,883 B2 | 11/2007 | De Felice et al. |
| 7,186,966 | B2 | 3/2007 | Al-Ali | 7,295,866 B2 | 11/2007 | Al-Ali |
| 7,190,261 | B2 | 3/2007 | Al-Ali | 7,328,053 B1 | 2/2008 | Diab et al. |
| 7,215,984 | B2 | 5/2007 | Diab et al. | 7,332,784 B2 | 2/2008 | Mills, et al. |
| 7,215,986 | B2 | 5/2007 | Diab et al. | 7,340,287 B2 | 3/2008 | Mason et al. |
| 7,221,971 | B2 | 5/2007 | Diab et al. | 7,341,559 B2 | 3/2008 | Schulz et al. |
| 7,225,006 | B2 | 5/2007 | Al-Ali et al. | 7,343,186 B2 | 3/2008 | Lamego et al. |
| 7,225,007 | B2 | 5/2007 | Al-Ali et al. | D566,282 S | 4/2008 | Al-Ali et al. |
| RE39,672 | E | 6/2007 | Shehada et al. | 7,355,512 B1 | 4/2008 | Al-Ali |
| 7,239,905 | B2 | 7/2007 | Kiani-Azarbayjany et al. | 2006/0215409 A1* | 9/2006 | Ohmi et al. ............ 362/341 |
| 7,245,953 | B1 | 7/2007 | Parker | 2008/0115350 A1* | 5/2008 | Kerr et al. ............ 29/832 |
| 7,254,431 | B2 | 8/2007 | Al-Ali et al. | | | |
| 7,254,433 | B2 | 8/2007 | Diab et al. | * cited by examiner | | |

DETECTOR SHIELD

PRIORITY CLAIM TO RELATED PROVISIONAL APPLICATIONS

The present application claims priority benefit under 35 U.S.C. §119(e) of U.S. Provisional Application Ser. No. 60/876,758, filed Dec. 22, 2006, entitled "Detector Shield," which is incorporated herein by reference.

FIELD OF THE INVENTION

The disclosure provided relates to the field of spectroscopy. More particularly, the disclosure relates to the field of photodiode detectors.

BACKGROUND

Spectroscopy is a technique for measuring the concentration of organic and inorganic constituents of a solution. A common application of this technique occurs in the field of pulse oximetry. Pulse oximetry is the noninvasive measurement of the oxygen saturation level of arterial blood. Early detection of low blood oxygen saturation is critical because an insufficient supply of oxygen can result in brain damage and death in a matter of minutes. The use of pulse oximetry in operating rooms and critical care settings is widely accepted. Pulse oximeters generally include a light source and a detector. The light source transmits light (typically red and infrared light) through body tissue where it is attenuated by the tissue. The detector detects the attenuated light and sends a signal indicative of the detected light to a patient monitor for analysis.

SUMMARY

A limitation in many detector applications is a background noise floor which masks the signal detected by the detector. A contributing factor to background noise in the detector circuit, as in most electronic circuits, is the parasitic coupling of electromagnetic interference (EMI) into the circuit. External sources of EMI vary from power lines and cellular telephones to medical devices such as diathermy, MRI and lasers. Conventionally, an electromagnetic shield is utilized as an effective method of reducing the effect of EMI-induced noise. Typical shielding techniques involve surrounding potentially affected parts with a "Faraday cage" of electrically conducting material. An example of such an EMI shield is described in U.S. Pat. No. 5,782,757 entitled "LOW NOISE OPTICAL PROBES," the entire disclosure of which is incorporated herein. One of the most common employed electrically conducting materials is Copper because of its low cost and excellent qualities as a conductor. Conducting materials, however, are typically opaque to optical signals. Hence, for photodiode applications, electromagnetic shields typically have consisted of conductive "screens" having optically transmissive openings.

A disadvantage to the use of copper EMI shields is that the light that reaches the photodiode covered by a copper EMI shield contains wavelengths slightly different from the desired wavelengths that are emitted by the LEDs and subsequently attenuated by the body tissue of a patient before reaching the photodiode. This is because copper and other electrically conducting materials, reflect various wavelengths of light unevenly. Specifically, copper has been found to reflect more light of "red" wavelengths (i.e. 620-750 nm) as compared with those of "blue" wavelengths (i.e. 450-495 nm). Because a portion of light reflected off the surface of the EMI shield bounces around the optically transmissive openings and ultimately reaches the photodiode, the light signal detected by the photodiode contains wavelengths slightly different from those in the light signal emitted by the LEDs and attenuated by body tissue.

Aspects of the present disclosure include a photodiode detector shield that does not affect the wavelengths of light reaching the photodiode to the extent that copper does. As previously discussed, copper EMI shields reflect light of slightly different wavelengths than those reflected off their surfaces. In the present disclosure, a layer of shiny, lustrous material (such as Nickel) is placed over a copper EMI shield used in a photodiode detector. Because of its color and reflective properties, this layer of material will reflect substantially equal amounts of light within a predetermined band of desired wavelengths (e.g., 350 nm-1100 nm). Thus, by placing this reflective coating over the EMI shield, there is a substantial reduction in the light that contacts the copper EMI shield layer. Because any light reflected off the outer nickel surface comprises largely the same wavelengths as the light which is emitted by LEDs and attenuated by the body tissue of a patient, the adverse effects of the copper shield are avoided.

Another aspect of the present disclosure is to provide a way of shielding a photodiode from electromagnetic interference and ambient light by using a multi-layered detector shield. The first layer of the detector shield is made from an electrically conductive material, such as copper or a copper alloy. This layer is shaped to fit over the photodiode in order to shield the photodiode from electromagnetic interference. The second layer of the detector shield is made from a shiny material which reflects light of substantially the same wavelengths as those which are emitted onto it, such as sulfamate nickel, pure nickel or a nickel alloy. The second layer is placed over the first layer in a manner that allows some light to pass through the layers unobstructed. Further, the two layers may be attached together it by welding, soldering, electroplating, wrapping, adhesively attaching the two layers, or using any other method of attaching the two layers. The two layers work together to shield the photodiode from electromagnetic interference without adversely affecting the wavelengths of light that reach the photodiode.

Yet another aspect of the present disclosure is to provide a method of making a detector shield by obtaining two layers of different materials, attaching the two layers together, and fitting both layers over a photodiode. The first layer is made from an electrically conductive material, such as copper or a copper alloy. The second layer is made from a shiny, material that reflects light of substantially the same wavelengths as those which are emitted onto it within a predetermined band of wavelengths. Such materials include nickel or nickel alloys, to name a few. The second layer is placed on top of the first layer to form an improved detector shield. The improved detector shield is fit over a photodiode, such as those that are used in pulse oximetry devices. The multilayered shield helps block electromagnetic interference from the photodiode without adversely affecting the wavelengths of light that reach the photodiode.

These and other features of the present disclosure are discussed or apparent in the following detailed description.

DETAILED DESCRIPTION OF THE PREFERRED EMBODIMENT

Figure 1:
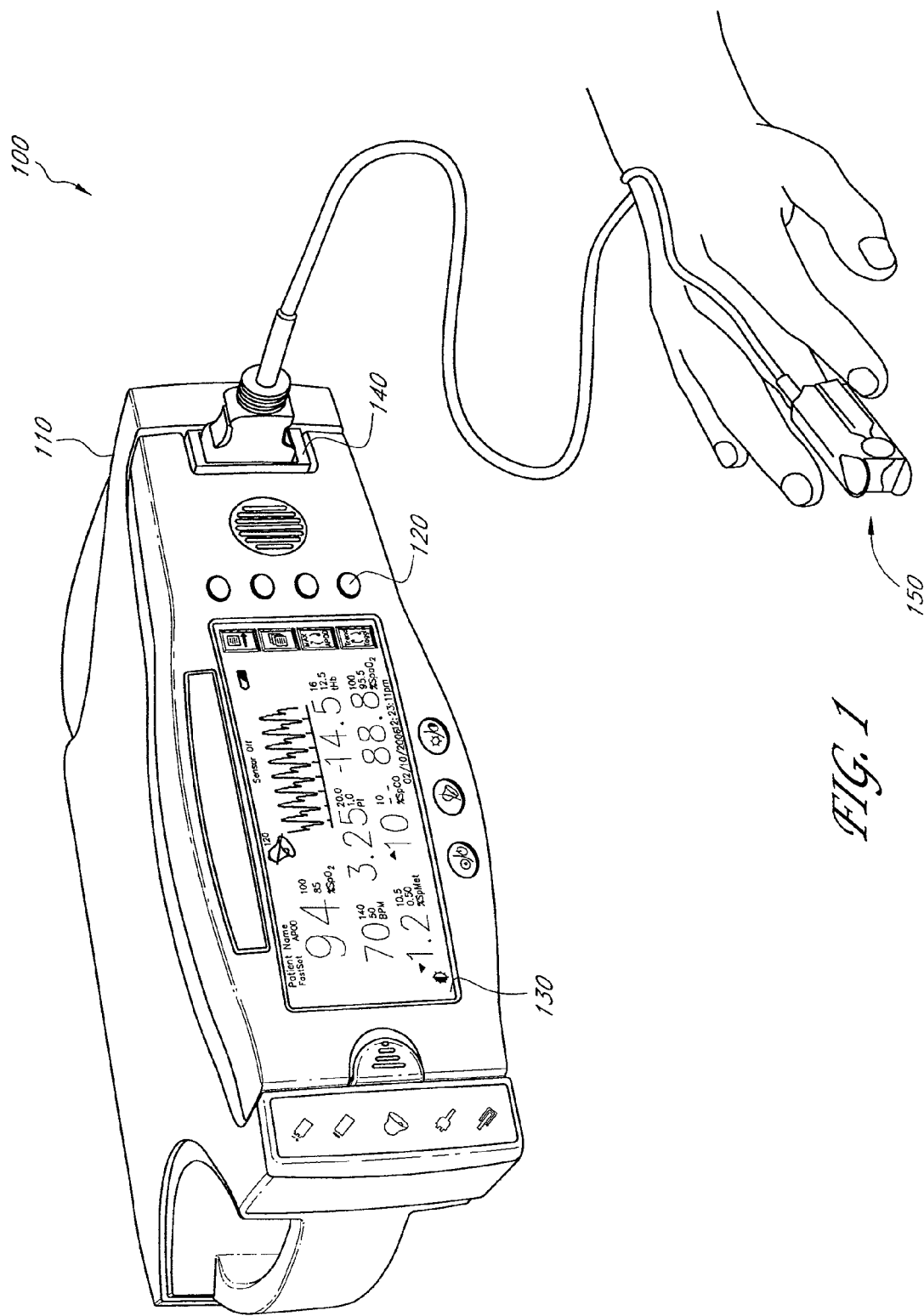
FIG. 1 is a perspective view of a physiological measurement system utilizing a sensor.

FIG. 1 illustrates a physiological measurement system 100 having a monitor 110 and a sensor assembly 150. The physiological measurement system 100 allows the monitoring of a person, including a patient. In particular, the sensor assembly 150 allows the measurement of a blood constituent and related parameters in addition to oxygen saturation and pulse rate, all with increased accuracy as compared with conventional pulse oximetry.

In one embodiment, the sensor assembly 150 is configured to plug into a monitor sensor port 140. Monitor keys 120 provide control over operating modes and alarms, to name a few. A display 130 provides readouts of measured parameters, such as oxygen saturation, pulse rate, HbCO and HbMet, to name a few.

Figure 2A:
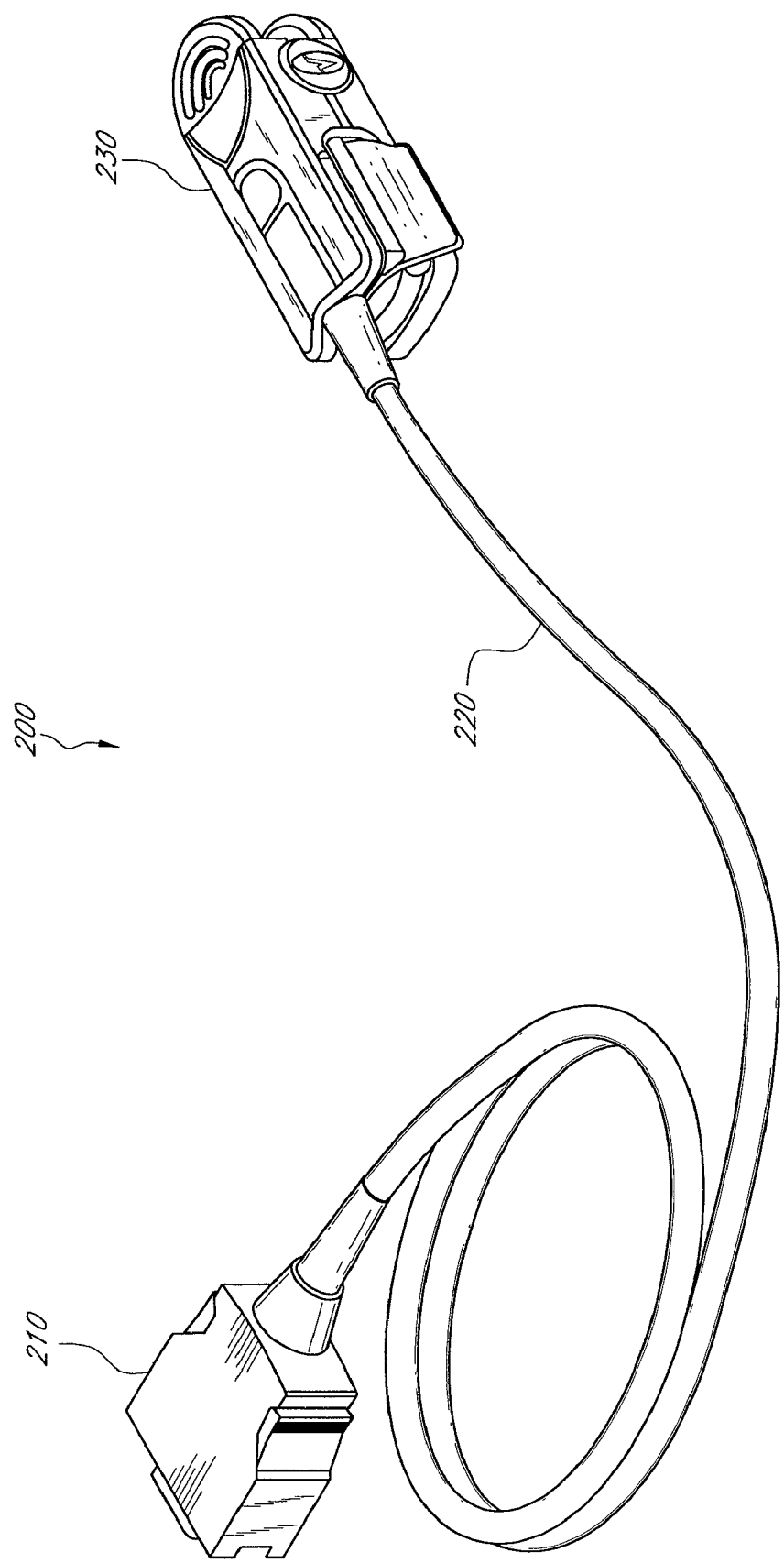
FIGS. 2A-C are perspective views of sensor embodiments.

FIG. 2A illustrates a sensor assembly 200 having a sensor 230 adapted to attach to the tissue site, a sensor cable 220 and a monitor connector 210. In one embodiment, the sensor 230 is incorporated into a reusable finger clip adapted to removably attach to, and transmit light (commonly red and infrared light) through a fingertip. The sensor cable 220 and monitor connector 210 are integral to the sensor 230, as shown. In alternative embodiments, the sensor 230 may be configured separately from the cable 220 and connector 210.

Figure 2B:
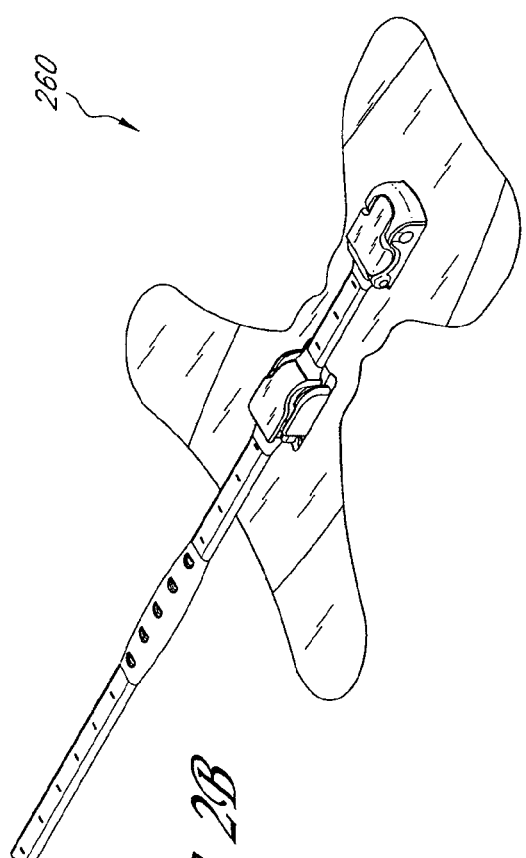
Figure 2C:
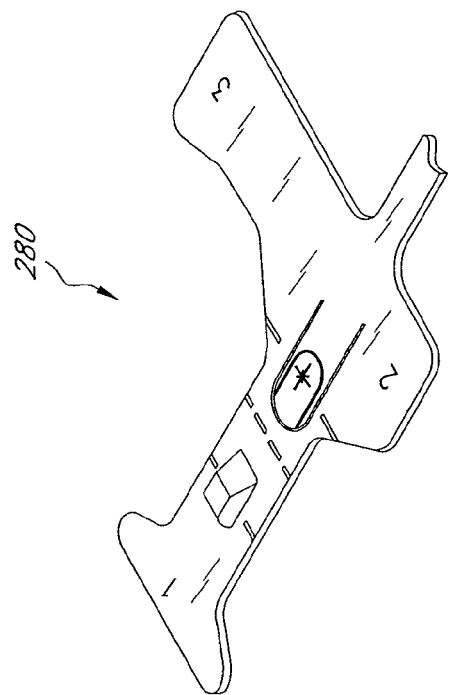

FIGS. 2B-C illustrate alternative sensor embodiments, including a sensor 260 (FIG. 2B) partially disposable and partially reusable (resposable) and utilizing an adhesive attachment mechanism. Also shown is a sensor 280 (FIG. 2C) being disposable and utilizing an adhesive attachment mechanism. In other embodiments, a sensor may be configured to attach to various tissue sites other than a finger, such as a foot or an ear. Also a sensor may be configured as a reflectance or transflectance device that attaches to a forehead or other tissue surface.

Figure 3:
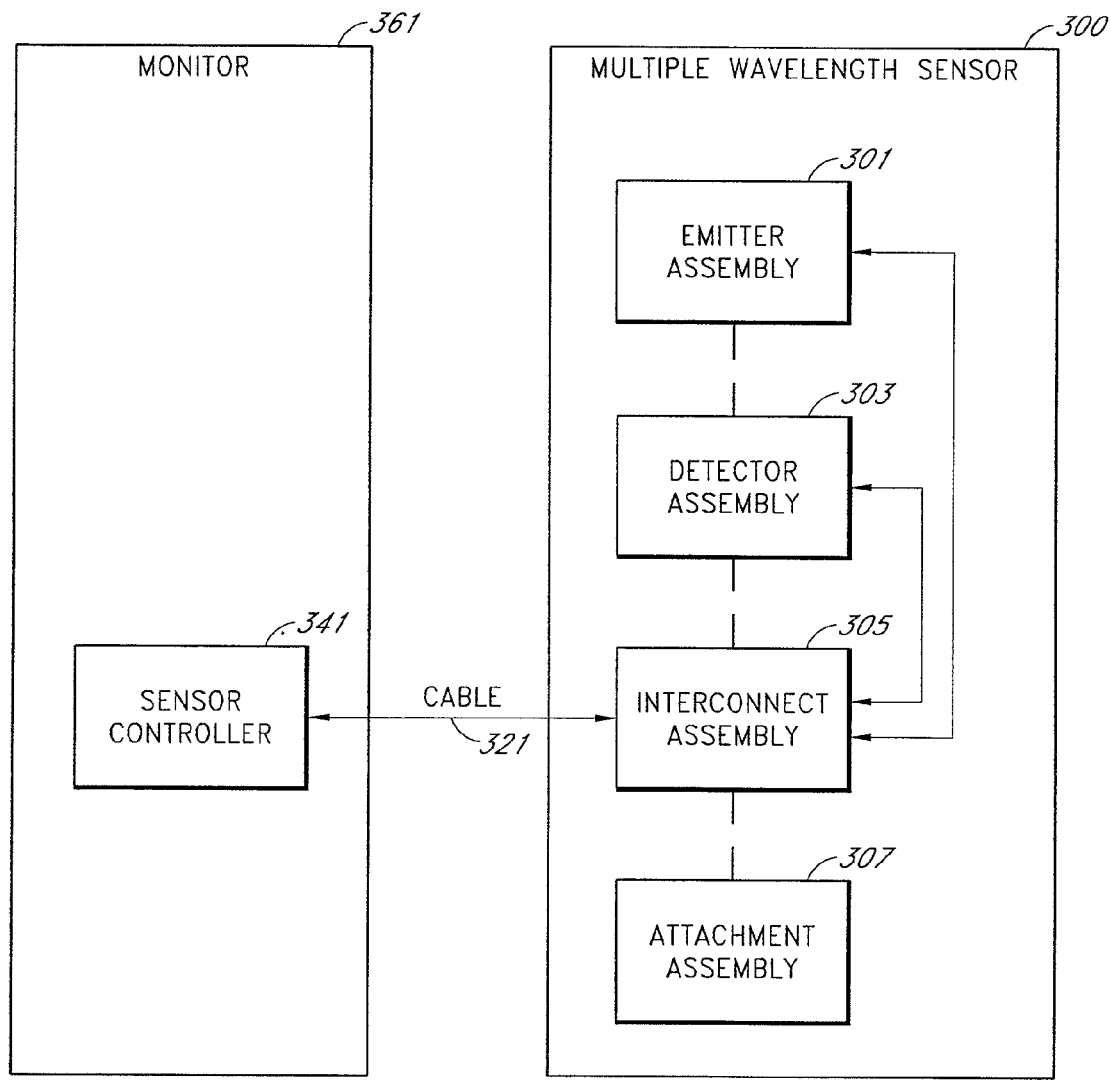
FIG. 3 is a general block diagram of a sensor and sensor controller.

FIG. 3 illustrates a sensor assembly 300 having an emitter assembly 301, a detector assembly 303, an interconnect assembly 305 and an attachment assembly 307. The emitter assembly 301 responds to drive signals received from a sensor controller 341 in the monitor 361 via the cable 321 so as to transmit optical radiation having a plurality of wavelengths into a tissue site. The detector assembly 303 provides a sensor signal to the monitor 361 via the cable 321 in response to optical radiation received after attenuation by the tissue site. The interconnect assembly 305 provides electrical communication between the cable 321 and both the emitter assembly 301 and the detector assembly 303. The attachment assembly 307 attaches the emitter assembly 301 and detector assembly 303 to a tissue site, as described above. The detector assembly 303 is described in further detail with respect to FIG. 5, below.

Figure 4:
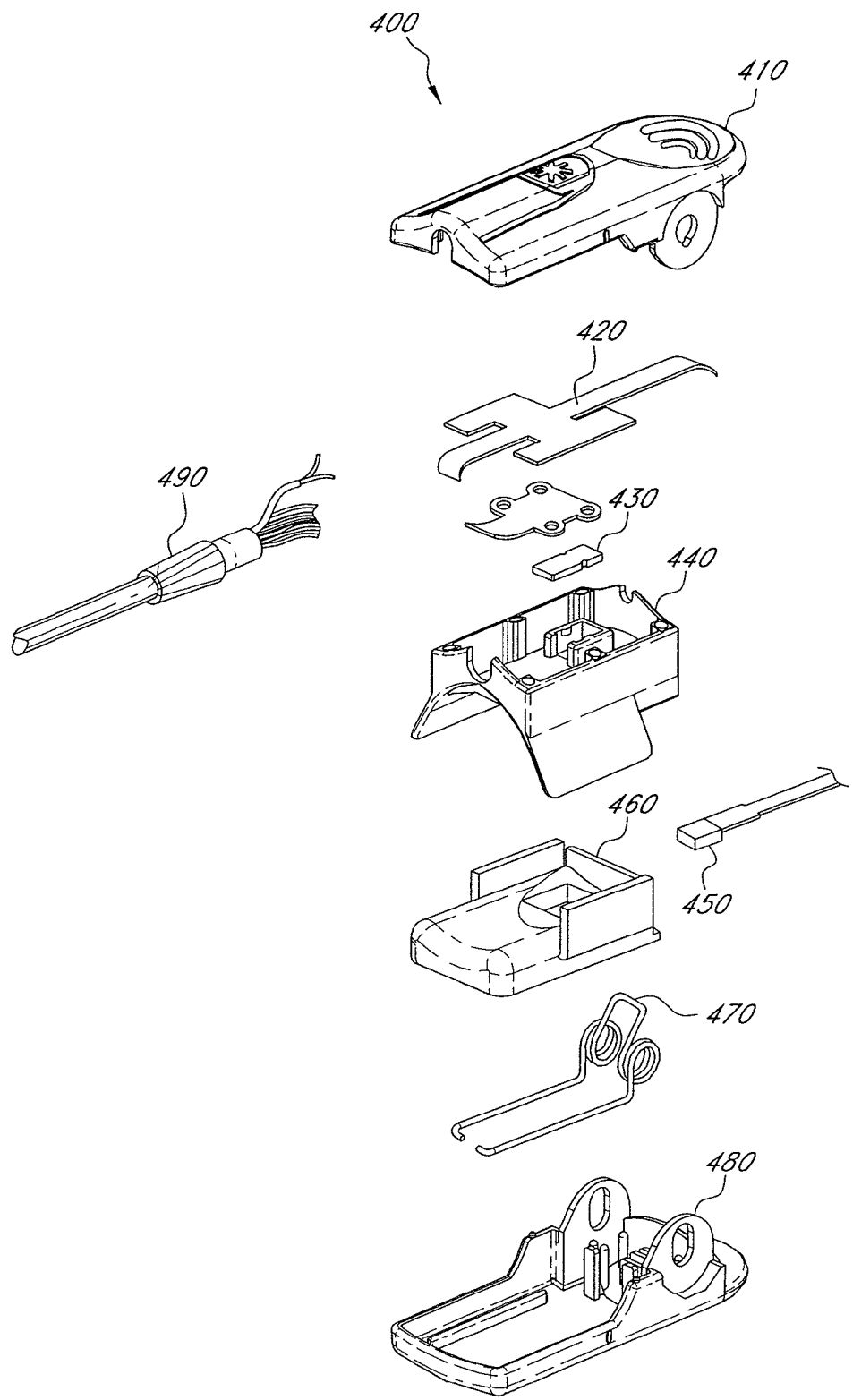
FIG. 4 is an exploded perspective view of a sensor embodiment.

FIG. 4 illustrates a sensor 400 embodiment that removably attaches to a fingertip. The sensor 400 houses a multiple wavelength emitter assembly 430 and corresponding detector assembly 450. A flex circuit assembly 420 mounts the emitter and detector assemblies 450 and interconnects them to a multi-wire sensor cable 490. Advantageously, the sensor 400 is configured in several respects for both wearer comfort and parameter measurement performance. The flex circuit assembly 420 is configured to mechanically decouple the cable 490 wires from the emitter and detector assemblies 450 to reduce pad stiffness and wearer discomfort. The pads 440, 460 are mechanically decoupled from shells 410, 480 to increase flexibility and wearer comfort. A spring 470 is configured in hinged shells 410, 480 so that the pivot point of the finger clip is well behind the fingertip, improving finger attachment and more evenly distributing the clip pressure along the finger. As shown in FIG. 4, the detector pad 460 is structured to properly position a fingertip in relationship to the detector assembly 450. The pads have flaps that block ambient light. The detector assembly 450 is housed in an enclosure so as to reduce light piping from the emitter assembly to the detector assembly without passing through fingertip tissue. Although described in relation to a preferred embodiment, it is to be understood by a person of ordinary skill in the art that the present disclosure is applicable to any physiological sensor having a photodiode. It is also to be understood by a person of ordinary skill in the art that although the present disclosure is described in relation to a preferred embodiment, the present disclosure is applicable to any detector assembly.

Figure 5:
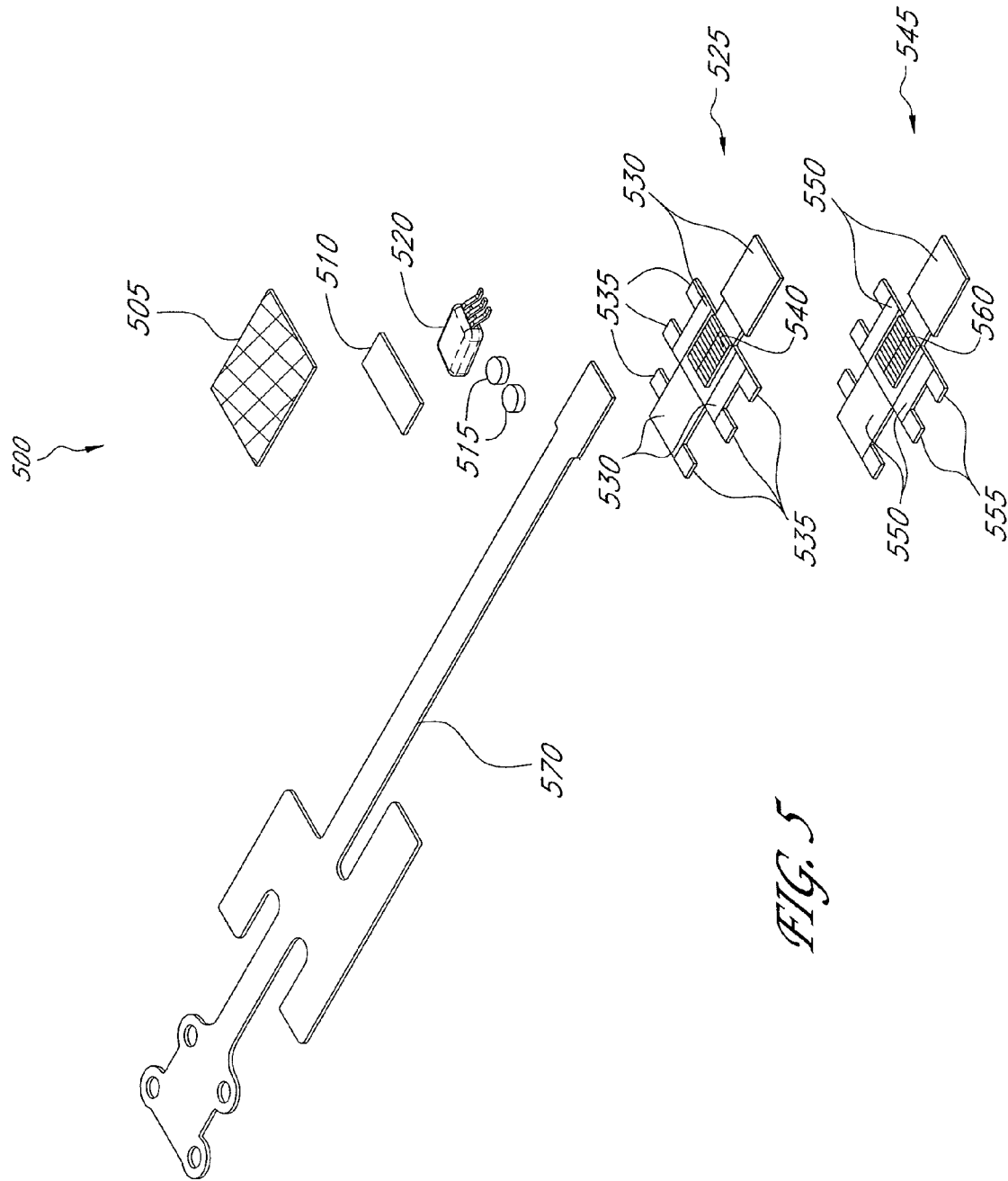
FIG. 5 is an exploded perspective view of detector assembly according to an embodiment of the present disclosure.

FIG. 5 illustrates an embodiment of a detector assembly 500 including a detector 520, detector solder pads 510, copper mesh tape 505, EMI shield 525, and shield plate 545. EMI shield 525 further includes EMI shield walls 530, EMI shield tabs 535, EMI shield grid 540. Shield plate 545 further includes shield plate walls 550, shield plate tabs 555, and shield plate grid 560. The detector 520 is soldered 515 chip side down to detector solder pads 510 of the flex circuit 570. The detector solder joint and detector ground pads 510 may be wrapped with tape. EMI shield tabs 535 are folded onto the detector pads 510 and soldered. The EMI shield walls 530 are folded around the detector 520 and the remaining tabs 535 are soldered to the back of the EMI shield 525. The copper mesh tape 505 is cut to size and the shielded detector and flex circuit solder joint are wrapped with the copper mesh tape 505. Shield plate 545 is placed over EMI shield 525 and shield plate grid 560 is aligned with EMI shield grid 540. Shield plate walls are bent and folded over EMI shield walls 530 and shield plate grid 560 is aligned with EMI shield grid 540.

In alternative embodiments, shield plate 545 can have a shape that is different from EMI shield 525. For example, it can be formed to cover only shield plate grid 560. Moreover, shield plate 545 and EMI shield 525 may be attached together by welding, soldering, electroplating, wrapping, using adhesive materials, or any other way of attaching the two layers. Alternatively, detector assembly 500 can further include a portion of foil, which would be cut to size with a predetermined aperture. The foil can be wrapped around the shielded detector with the foil side in and the aperture aligned with the EMI shield and shield plate grids.

Figure 6:
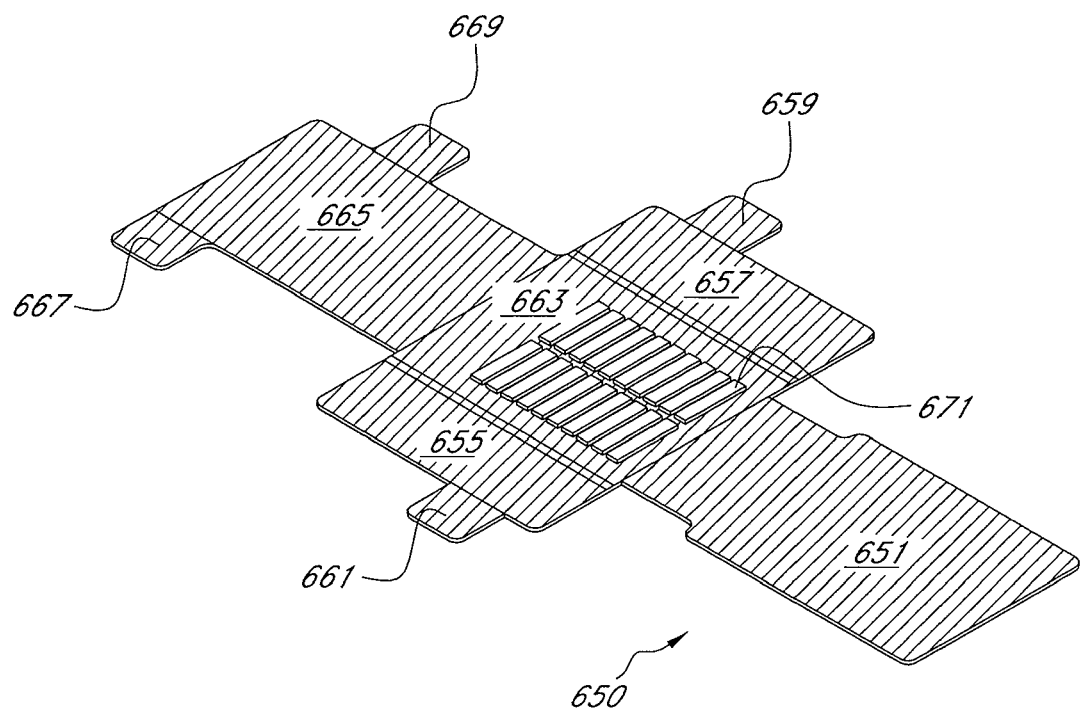
FIG. 6 is an exploded perspective view of a detector shield according to an embodiment of the present disclosure.
Figure 6:
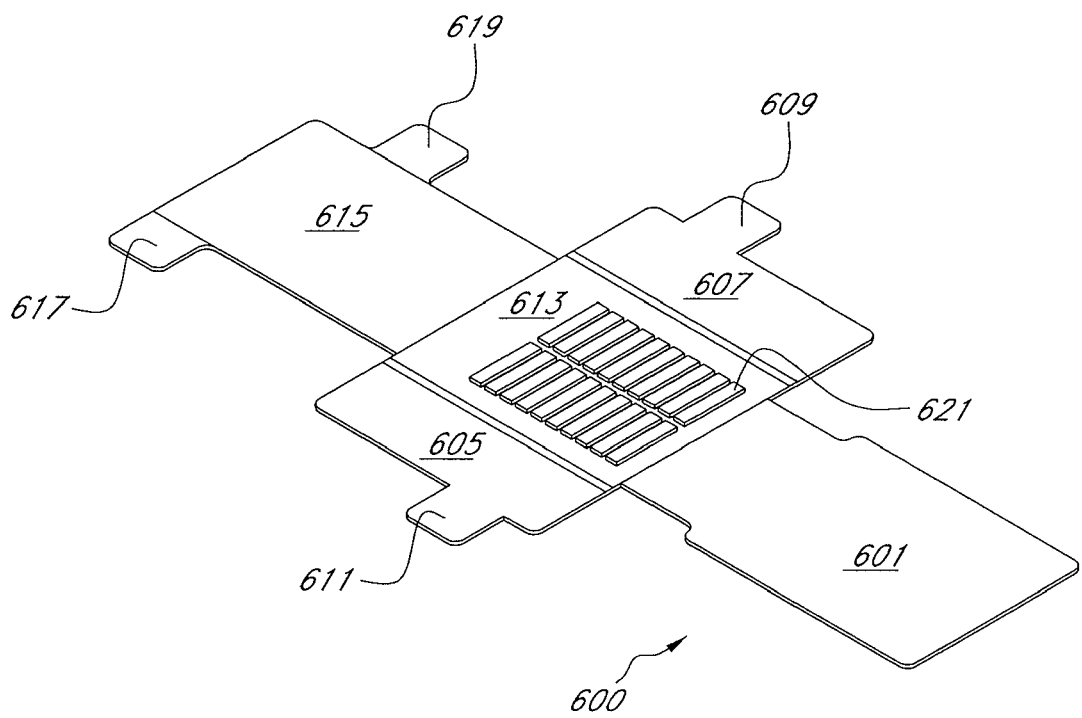

FIG. 6 shows an exploded view of an embodiment of the detector shield. The detector shield includes EMI shield 600 and shield plate 650. EMI shield 600 is made from an electrically conducting material, such as copper or a copper alloy, in order to keep various forms of electromagnetic interference from penetrating its structure. The EMI shield 600 includes EMI shield walls 601, 605, 615, and 617, and EMI shield tabs 607, 609, 611, and 613. EMI shield walls 601, 605, 615, and 617 are malleable and thus may be folded downward around a photodiode, blocking the photodiode from electromagnetic interference as well as ambient light. EMI shield 600 further includes EMI shield grid 613. EMI shield grid 613 includes slots 621. These slots are openings in the EMI shield that allow for the unobstructed passage of light. This unobstructed light ultimately will reach the photodiode.

Shield plate 650 includes shield plate grid 663, walls 651, 655, 657, and 665, and tabs 659, 661, 667, and 669. The shield plate grid includes slots 671. The various parts of the shield plate 650 are designed to be in substantially conformity with corresponding parts of the EMI shield 600. Shield plate 650 is preferably made from nickel, sulfamate nickel, or a nickel alloy. This is because the reflective properties of nickel and its color (silvery white) make it such that light is substantially evenly reflected within a desired band of wavelength. Furthermore, nickel is a relatively soft metal, thus allowing bending and malleability of the material without substantial probability of cracking the material. In one embodiment, a sulfamate nickel shield plate can have a thickness of about $30-50 \times 10^{-6}$ inches. However, the thickness of shield plate 750 may vary, as may be appreciated by those of ordinary skill in the art.

In the improved detector shield of FIG. 6, shield plate 650 is placed over EMI shield 600 such that the various parts of shield plate 650 cover corresponding parts of the EMI shield. Thus, for example, shield plate walls 651, 655, 657, and 665 may be aligned to cover walls 601, 605, 607, and 615 of EMI shield 600. Likewise, shield grid 663 would substantially cover EMI shield grid 613. EMI shield 600 can also be attached to shield plate 650 by various means such as welding, soldering, electroplating, wrapping, or using adhesive material(s).

As may be recognized by those of ordinary skill in the art, EMI shield 600 may be made of electrically conducting materials other than copper or copper alloys. Also, shield plate 650 may be made of other materials with reflective properties and/or colors similar to those of sulfamate nickel, pure nickel and nickel alloys. Specifically, the shield plate can be substantially made from alternative materials that do not reflect "red" colors like copper does. In alternative embodiments, the shield plate may be less than $30 \times 10^{-6}$ inches thick or greater than $50 \times 10^{-6}$ inches thick. In one embodiment, the shield plate may be constructed to cover less or more than the entire EMI shield. For example, the shield plate can have dimensions that would substantially cover only EMI shield grid 613. In such an embodiment, the shield plate can be attached to the EMI shield by various methods such as welding, wrapping, using adhesive materials, or other forms of attachment, as may be appreciated by one of skill in the art. Furthermore, EMI shield 600 and shield plate 650 may include one slot or opening instead of multiple slots for the unobstructed passage of light.

Figure 7A:
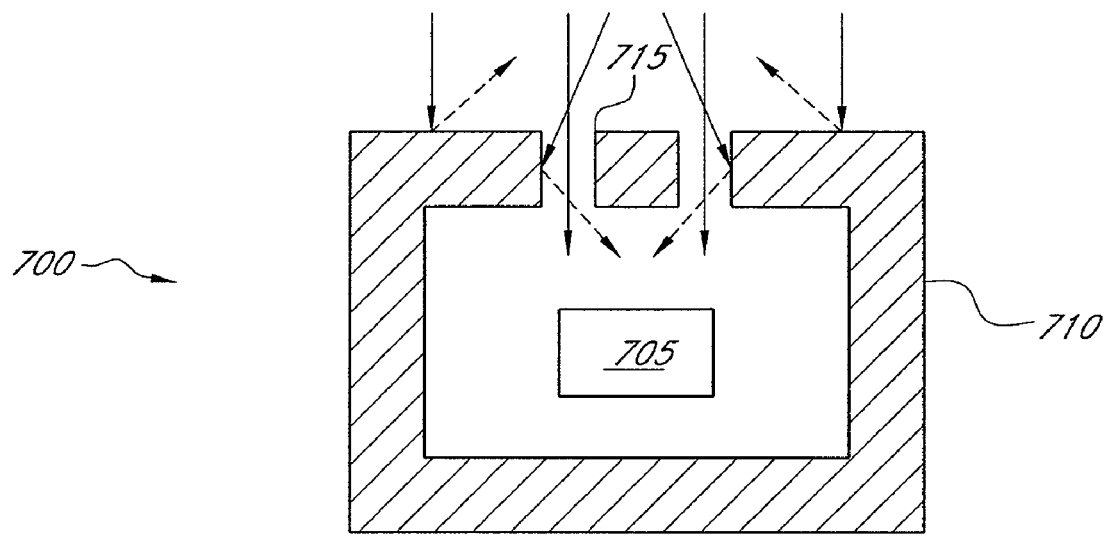
FIG. 7A is a cross sectional view of a detector utilizing a copper shield.

FIG. 7A presents a cross-sectional view of detector 700. Detector 700 includes photodiode 710 and copper EMI shield 720, which substantially encloses photodiode 710. Copper EMI shield 720 further includes a plurality of slots 730. Copper EMI shield 720 is folded around photodiode 710. In this regard, the EMI shield acts as a "Faraday cage" of conducting material surrounding the photodiode and forms a shield to reduce the effect of EMI-induced noise.

As previously mentioned, an aspect to the electromagnetic shielding that copper provides is its uneven reflectivity of different wavelengths of light. Due to its color, copper has been found to have a greater reflectivity of light of "red" wavelengths (i.e. 620-750 nm) as compared to those of "blue" wavelengths (i.e. 450-495 nm).

This uneven reflectivity can affect the spectral response of the photodiode because a portion of the light that is reflected from the surface of the copper EMI shield ultimately can reach the photodiode. Thus, the photodiode is exposed to more light of red wavelengths than desired. This affects the response of the photodiode because it is being exposed to a greater amount of "red" light than light of other wavelengths.

In operation, light attenuated by body tissue is emitted onto prior art detector 700. As seen in FIG. 7A, a portion of the attenuated light is unobstructed and passes through slots 715, reaching photodiode 705. The remainder of the light is reflected off the surface of the EMI shield 710, preferably made from copper in order to block electromagnetic interference. The reflected light is denoted by the dotted-lined arrows. A portion of this reflected light bounces around the openings of slots 715, and reaches the photodiode 705, which sends an electrical signal indicative of the light it detects to a processor (not shown) for analysis. As discussed earlier, copper EMI shield 710 reflects more light of certain wavelengths as compared to those of other wavelengths. Thus, the light that reaches the photodiode 705 includes both unreflected light (denoted by the solid-arrows touching upon photodiode 705), as well as light that has been reflected from the surface of the copper EMI shield 710. This can result in a spectrum of light that is slightly different from that which is desired, hence affecting the spectral response of the photodiode 705.

Figure 7B:
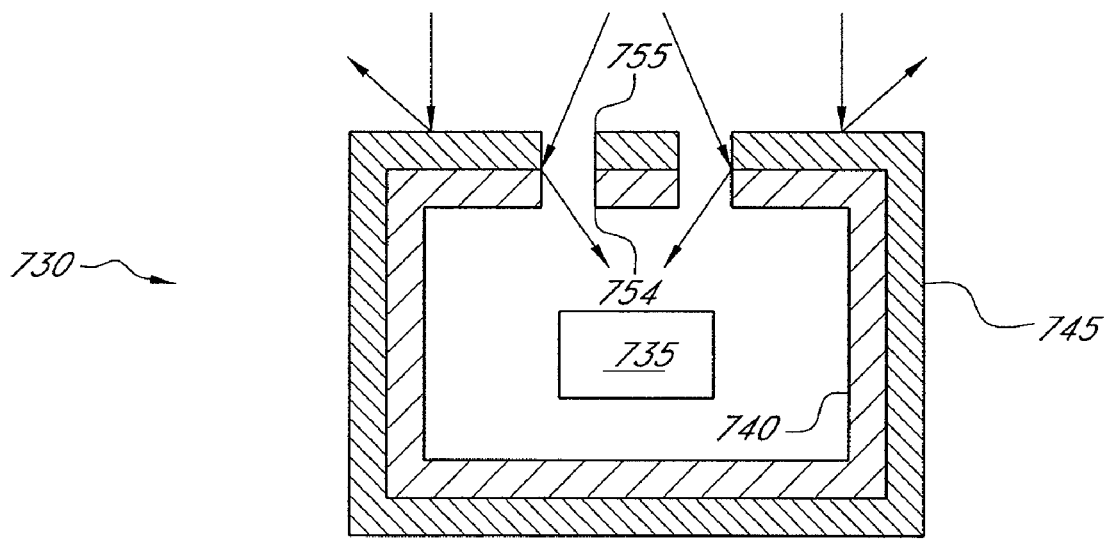
FIG. 7B is a cross-sectional view of a detector utilizing a detector shield according to an embodiment of the present disclosure.
Figure 8A:
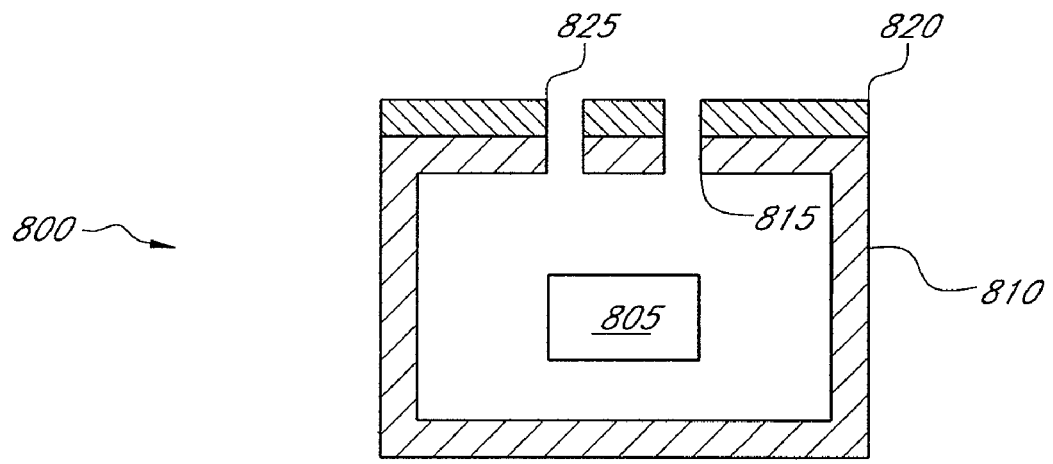
FIGS. 8A-D are cross-sectional views of detectors utilizing detector shields according to various alternative embodiments of the present disclosure.
Figure 8B:
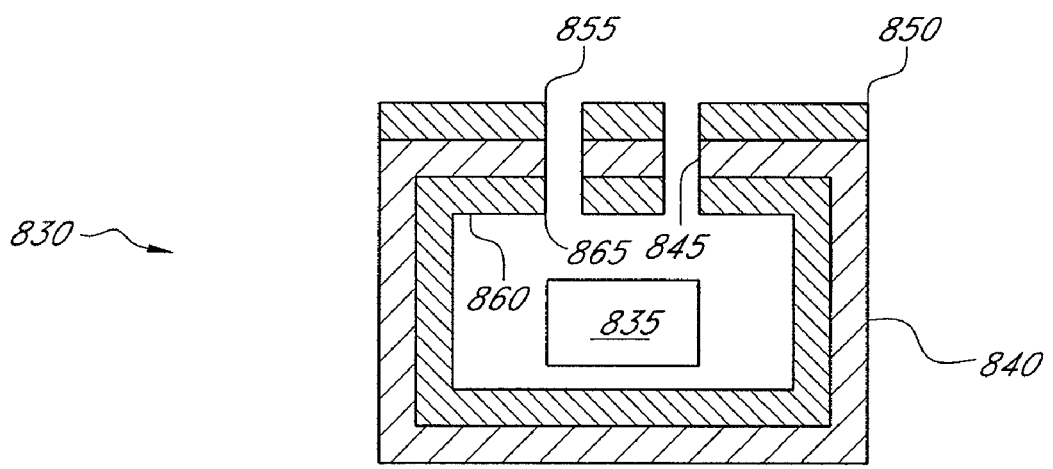
Figure 8C:
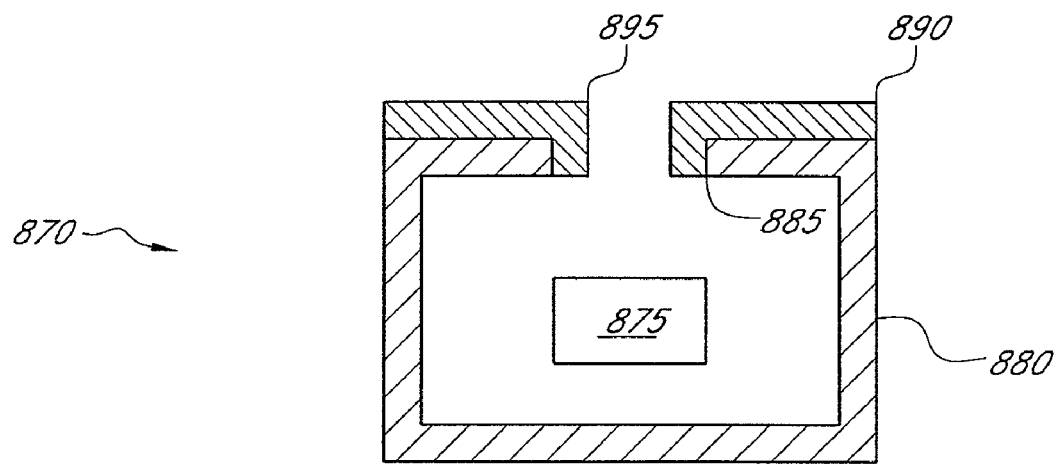
Figure 8D:
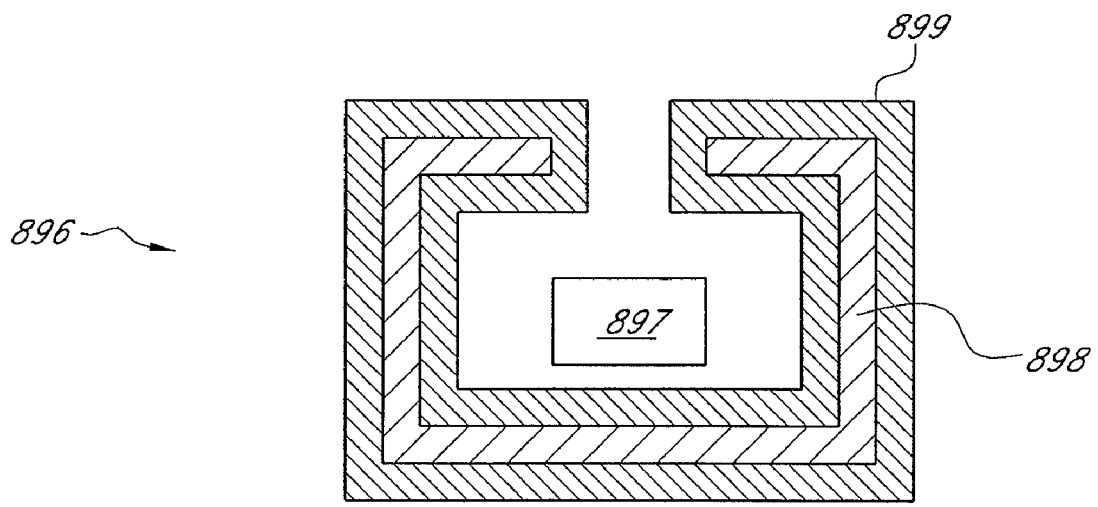

FIG. 7B presents a cross sectional view of a detector 730 with an improved detector shield according to an embodiment of the present disclosure. Improved detector 730 includes photodiode 735, copper EMI shield 740, and shield plate 745. Copper EMI shield 740 and shield plate 745 both include a plurality of slots 754 and 755, respectively. The shield plate, preferably made from sulfamate nickel, is placed on top of copper EMI shield 740 in such a manner as to substantially align slots 754 and 755. The new combination will fit onto a photodiode 735 in such manner as to substantially enclose it.

In operation, light attenuated by body tissue is emitted onto improved detector 730. This attenuated light will first come into contact with shield plate 745. Slots 754 and 755, due to their substantial alignment, will allow a portion of the attenuated light to pass directly to photodiode 735, unobstructed by the shield plate 745 or the EMI shield 740. Shield plate 745 reflects a portion of the attenuated light away from the shield plate. Some of the light reflected from the shield plate 745, however, may pass through the slots 754 and/or 755, and reach photodiode 735. As previously described, shield plate 745 is preferably made from sulfamate nickel. Because of its reflective qualities and silvery-white color which takes a high polish, the sulfamate nickel shield plate reflects light of various wavelengths relatively evenly across a predetermined bandwidth of wavelengths, such as from 350 nm-1100 nm. Thus, any reflected light that may pass through slots 754 and or 755 will be of substantially the same wavelengths of the desired, unobstructed light (e.g., red light), indicated by the solid arrows touching upon the photodiode. This reduces the adverse effects of the copper EMI shield, which in turn, improves the accuracy of the signal sent by the photodiode detector.

While some embodiments of improved detector 730 include a shield plate 745 and copper EMI shield 740 including a plurality of slots 754 and 755 respectively, a single slot or opening may also be used. Also, shield plate 745 may be sized to fit over a portion of EMI shield 740, instead of the entire shield. Further, shield plate 745 can be made from elements or compounds that have colors and/or exhibit similar reflective properties similar to that of sulfamate nickel, such as pure nickel, a nickel alloy, palladium, or platinum, to name a few. Copper EMI shield 740 may be substantially made from electrically conducting materials that can shield induced electromagnetic forces, other than pure copper. Such materials can include chalcocite, silver, or a silver alloy, to name a few. Also, those of ordinary skill in the art will understand that any type of photodiode can be used, such as a PIN, PN, or avalanche diode. Further, EMI shield and shield plate may be attached together by soldering, electroplating, welding, wrapping, or using an adhesive material the two layers together, or by any other means that will effectively attach the two layers together to form the improved detector shield.

FIGS. 8 A-D illustrate alternative embodiments of photodiode detectors utilizing detector shields. FIG. 8A illustrates photodiode detector embodiment 800, which includes photodiode 805, EMI shield 810 and shield plate 820. EMI shield 810 and shield plate 820 further include slots 815 and 825, respectively. In this embodiment, shield plate 820 covers only the top surface of EMI shield 810. An advantage to this alternative embodiment is a savings in production costs because less material is used. Light attenuated by body tissue will be transmitted towards the shield plate 820 in the same manner as previously described with respect to FIG. 7B. A portion of the light that does not pass directly through slots 815 and 825 will be reflected off the surface of shield plate 820, which is preferably made from sulfamate nickel or another material with similar color and/or reflective properties. The reflected light will include substantially the same wavelengths as the light emitted onto the surface of shield plate 820. Any portion of the reflected light to reach the photodiode will thus include substantially the same wavelengths as that of the attenuated light transmitted toward the surface of shield plate 820.

FIG. 8 B illustrates photodiode detector embodiment 830, which includes photodiode 835, EMI shield 840, top shield plate 850 and bottom shield plate 860. EMI shield 840 further includes slots 845. Top and bottom shield plates 850 and 860 further include slots 855 and 865, respectively. Thus, in this embodiment, both the top and bottom side of the top surface of EMI shield 840 is coated with a shield plate layer, preferably made from sulfamate nickel. An advantage to this design is that any light reflecting off an inside surface of the EMI shield will be reflecting off the sulfamate nickel shield plate before reaching photodiode 835.

FIG. 8 C illustrates photodiode detector embodiment 870, which includes photodiode 875, EMI shield 880 and sulfamate nickel shield plate 890. EMI shield 880 and shield plate 890 include slot 885 and 895. The dimensions of slot 885 and 895 are different such that shield plate layer 890 can substantially cover the ridges of slot 885, as shown in FIG. 8C. As previously explained, the EMI shield is made substantially from copper, which exhibits uneven reflective properties light of different wavelengths. An advantage to the embodiment presented in FIG. 8 C is that covering the ridges of slot 885 eliminates the possibility of any incident light being reflected off the surface of the ridges.

FIG. 8 D illustrates photodiode detector embodiment 896, which includes photodiode 897, EMI shield 898 and sulfamate nickel shield plate 899. As seen in the figure, shield plate 899 covers the top surface, bottom surface, and any ridge of any optically transmissive opening of EMI shield 898. An advantage to the embodiment presented in FIG. 8 C is that covering all surfaces of the EMI shield 898 substantially eliminates all possibility of light contacting the copper EMI surface. As may appreciated by those of ordinary skill in the art, however, a combination of configurations as well as other configurations of coating the EMI shield also are effective in negating the affect the copper shield will have on certain wavelengths of light.

Figure 9A:
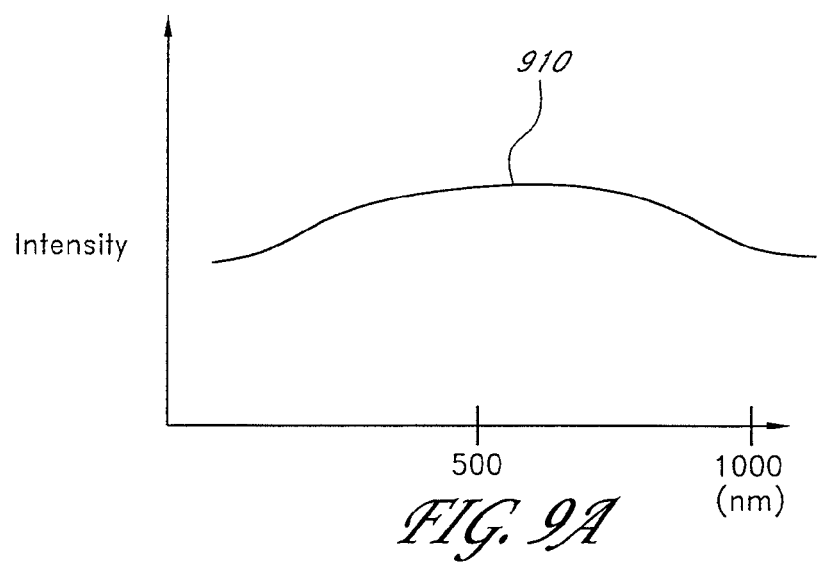
FIG. 9A is a graph of an ideal photodiode spectral response.

FIGS. 9 A-C depict graphs of photodiode spectral responses to light of various wavelengths attenuated by body tissue. Specifically, FIG. 9A depicts the ideal photodiode response of a detector without EMI shielding or interference. The spectral response graph includes an x-axis indicating wavelength and a y-axis indicating the intensity of the attenuated light signal which is detected by the photodiode. As shown in FIG. 9A, the ideal spectral response curve 910 of the photodiode is relatively flat. This means that the photodiode is receiving substantially equal amounts of light of light of varying wavelengths, such as light of red and infrared wavelengths. Although this is the ideal response curve, in many clinical situations, electromagnetic interference (EMI) distorts the accuracy of the photodiode response, necessitating an EMI shielding device to shield the photodiode from electromagnetic interference of various kinds.

Figure 9B:
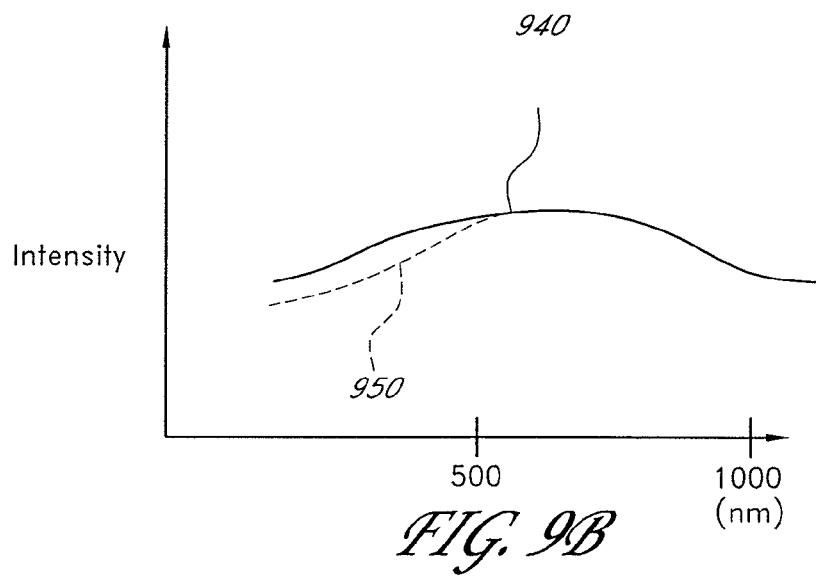
FIG. 9B is a graph of an ideal photodiode spectral response superimposed onto a spectral response of a photodiode with a copper shield.

FIG. 9B illustrates the respective responses of an ideal photodiode without EMI shielding or electromagnetic interference and a photodiode detector using an EMI shield made from copper. The spectral response graph includes an x-axis indicating wavelength and a y-axis indicating the intensity of the attenuated light signal which is detected by the photodiode. As seen in FIG. 9B, the ideal spectral response curve 940 is relatively flat across the spectrum of light depicted in the graph, specifically, from approximately 400 nanometers to 1000 nanometers. Use of a photodiode detector with prior art EMI shielding, such as those made from copper, results in prior art spectral response curve 950, which is slightly different from the ideal response. In particular, the intensity of the response is lower for wavelengths from approximately 400 nm to 500 nm, a result of the uneven reflectivity of light by the prior art EMI shields, as discussed above.

Figure 9C:
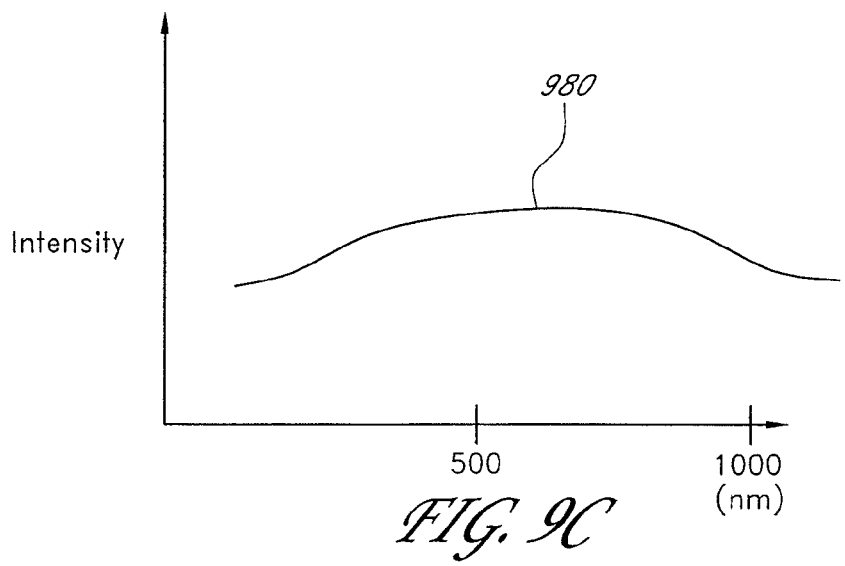
FIG. 9C is a graph of the spectral response of a photodiode with an improved detector shield according to an embodiment of the present disclosure.

FIG. 9C illustrates the spectral response curve for a photodiode detector with an improved detector shield according to various embodiments presented. Again, the spectral response graph includes an x-axis indicating wavelength and a y-axis indicating the intensity of the attenuated light signal which is detected by the photodiode. As seen in FIG. 9C, improved spectral response curve 980 of a photodiode with an improved detector shield is relatively flat, thus exhibiting behavior similar to that of the ideal spectral response curve as discussed with respect to FIG. 9A. This is because the shield plate, made of nickel or other element(s) with similar color and reflective qualities, reflects incident light substantially evenly across various wavelengths. Some of this reflected light, as discusses earlier, reaches the photodiode. The slots in the nickel shield plate, aligned with the similar slots in the copper EMI shield, allow for some of the attenuated light to pass through the improved detector shield unobstructed and come into contact with the photodiode. This attenuated light that is detected by the photodiode is not substantially affected by the uneven reflectivity of the EMI shield. Thus, the use of an improved detector shield according to embodiments of the present disclosure allow for a more accurate detection of the intensity of light of various wavelengths as compared to the spectral response of photodiodes using copper EMI shields.

Figure 10:
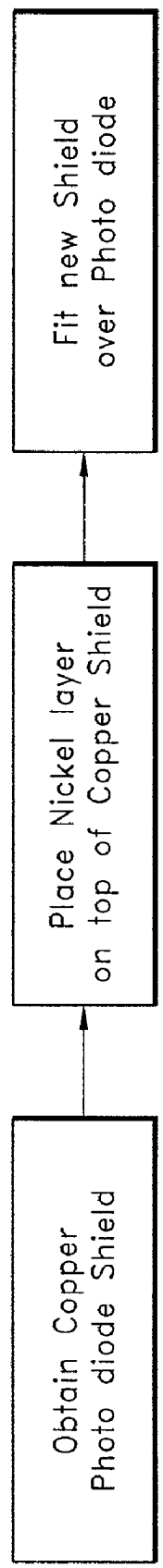
FIG. 10 is a flow chart of a method of making an improved photodiode detector shield according to an embodiment of the present disclosure.

FIG. 10 is a flow chart that illustrates the process of making an improved detector shield according to an embodiment of the present disclosure. First, an EMI shield, such as the copper one discussed earlier, is obtained. Next, a sulfamate nickel shield plate, cut to fit over the EMI shield, is placed over the EMI shield, with the slots of each layer being in substantially alignment. These two layers form the improved detector shield, which is fitted over a photodiode in a detector assembly, for example. As previously explained, the two layers may be attached together by using techniques such as welding, wrapping, soldering, electroplating, or using an adhesive substance.

Alternatively, the prior art EMI shield may be fitted over a photodiode before adding the nickel layer to the copper shield. Also, two sulfamate nickel shield plates may be utilized in making the detector shield. In this regard, one layer of sulfamate nickel is placed over the copper EMI shield and one layer is placed under the EMI shield before the detector is fit over a photodiode. Moreover, the sulfamate nickel shield plate may be obtained and cut before the EMI shield is obtained. The copper may also be bathed in liquid sulfamate nickel to coat the copper. As previously discussed, the EMI shield may be made substantially from elements and/or compounds other than copper that exhibit similar properties of shielding induced electromagnetic forces. Also, as may be appreciated by those of skill in the art, the shield plate may be made substantially from elements and/or compounds other than nickel that exhibit reflective properties similar to those of displayed by sulfamate nickel.

While particular elements, embodiments, and applications of the present invention have been shown and described, it is understood that the invention is not limited thereto since modifications may be made by those of ordinary skill in the art, particularly in light of the foregoing teaching. It is therefore contemplated by the appended claimed to cover such modifications and incorporate those features which come within the spirit and scope of the disclosure.

What is claimed is:

1. A photodiode detector shield for use in a physiological sensor, said shield comprising:
   a first layer of a detector shield comprising an electrically conductive material, said first layer including an optically transmissive area;
   a second layer of said detector shield comprising a material which reflects light of a predetermined band of wavelengths substantially evenly throughout the predetermined band;
   a faraday cage; said second layer comprising at least a portion of an outer layer of said cage;
   wherein said second layer combines with said first layer to substantially reduces light from contacting said first layer during optical measurements.

2. The detector shield of claim 1, wherein said electrical conducting material comprises copper.

3. The detector shield of claim 1, wherein said second material comprises a reflective finish.

4. The detector shield of claim 3, wherein said second material comprises nickel.

5. The detector shield of claim 3, wherein said second material comprises sulfamate nickel.

6. The detector shield of claim 1, wherein said optically transmissive area includes at least one slot for the transmission of light.

7. The detector shield of claim 1, wherein said second layer is attached to said first layer.

8. The detector shield of claim 7, wherein the second layer is attached by one or more of welding, adhesives, electroplating, and wrapping.

9. The detector shield of claim 1 further comprising a third layer comprising said second material, wherein said first layer is at least partially covered by second and third layers.

10. The detector shield of claim 1, wherein said band of wavelengths is from 350 nm-1100 nm.

11. A method of assembling an improved detector for use in a physiological sensor, said method comprising:
    providing a first layer of a detector shield, said first layer comprising a conductive material configured to block electromagnetic interference;
    providing a second layer of a detector shield, said second layer comprising a lustrous material that substantially evenly reflects various wavelengths of incident light;
    providing a faraday cage, said second layer comprising at least a portion of an outer layer of said cage;
    at least partially covering said first layer with said second layer;
    at least partially covering a photodiode with said first and second layers.

12. The method of claim 11, further comprising the step of attaching said second layer to said first layer.

13. The method of claim 11, further comprising the step of creating an optically transmissive area on said first and second layers that allows for the passage of light.

14. The method of claim 11, wherein at least partially covering said first layer with said second layer further comprises aligning said first and second layers such that said optically transmissive areas of both layers are in substantial alignment.

15. The method of claim 11 further comprising the step of providing a third layer, said third layer comprising said second material and at least partially covering said first layer.

16. A photodiode detector shield for use in a physiological sensor, said shield comprising:
    a first layer of a detector shield comprising an electrically conductive material, said first layer comprising an optically transmissive area;
    a layering means for at least partially covering said first layer, said layering means configured to reflect a predetermined band of wavelength substantially evenly throughout the predetermined band, said layering means comprising an optically transmissive area; and
    a faraday cage, said layering means comprising at least a portion of an outer layer of said cage.

* * * * *

UNITED STATES PATENT AND TRADEMARK OFFICE
CERTIFICATE OF CORRECTION

| | | |
|---|---|---|
| PATENT NO. | : 7,791,155 B2 | Page 1 of 1 |
| APPLICATION NO. | : 11/963518 | |
| DATED | : September 7, 2010 | |
| INVENTOR(S) | : Mohamed K. Diab | |

It is certified that error appears in the above-identified patent and that said Letters Patent is hereby corrected as shown below:

Column 5, Line 54, please change "30×100^-6" to --30×10^-6--.

Column 5, Line 55, please change "50×100^-6" to --50×10^-6--.

Signed and Sealed this
Twenty-second Day of November, 2011

David J. Kappos
*Director of the United States Patent and Trademark Office*